United States Patent [19]

Larkin

[11] 4,105,701

[45] Aug. 8, 1978

[54] PURIFICATION OF MATERIALS CONTAINING CARBONYL CONTAMINANTS

[75] Inventor: Donald R. Larkin, Corpus Christi, Tex.

[73] Assignee: Celanese Corporation, New York, N.Y.

[21] Appl. No.: 572,238

[22] Filed: Apr. 28, 1975

[51] Int. Cl.² .............. C07C 17/38; C07C 67/48; C07C 29/24
[52] U.S. Cl. .................. 260/650 R; 560/79; 560/248; 568/868; 568/870
[58] Field of Search ........... 260/475 PR, 499, 637 R, 260/637 A, 67 UA, 650 R; 526/9

[56] References Cited

U.S. PATENT DOCUMENTS

| 2,615,812 | 10/1952 | Kaufman | 260/637 R |
|---|---|---|---|
| 2,997,495 | 8/1961 | Rutledge et al. | 260/499 |
| 3,652,649 | 3/1972 | Woo et al. | 260/475 PR |
| 3,963,618 | 6/1976 | Muir | 526/9 |

FOREIGN PATENT DOCUMENTS

39/17,064  8/1964  Japan ............................................. 526/9

OTHER PUBLICATIONS

Tyurenkova et al., As Cited in Chem. Abstracts, 81, p. 159410c, (1974).
Kirk–Othmer, Encyclopedia of Chemical Technology, vol. 21, pp. 304–317, 2nd Edition (1970).
Roberts et al., *Basic Principles of Organic Chemistry*, p. 384-404, 443-447 (1964).
Rankin et al., as cited in C.A., 75, p. 53563r (1971).
Wagner et al., *Synthetic Organic Chemistry*, pp. 261–262, (1965).

*Primary Examiner*—Jane S. Myers
*Attorney, Agent, or Firm*—Ralph M. Pritchett

[57] ABSTRACT

A liquid contaminated with a carbonyl compound, especially an aldehyde, is purified by being contacted with a bed of solid polyvinyl alcohol particles or fibers. The carbonyl compound is adsorbed or chemisorbed onto the solid polyvinyl alcohol surface with resulting reaction in the carbonyl content of the liquid.

5 Claims, No Drawings

PURIFICATION OF MATERIALS CONTAINING CARBONYL CONTAMINANTS

BACKGROUND OF THE INVENTION

Contamination of organic compounds by carbonyl compounds, especially aldehydes, is a particular problem in the manufacture and utilization of humectants, food additives, and preservatives (e.g., glycerine, 1,3-propanediol, and 1,3-butanediol) and also in the manufacture of fiber or plastics monomers such as bis-(hydroxyethyl) terephthalate. Where use of the material in foods, pharmaceuticals, cosmetics, etc. is contemplated, very small quantities of carbonyl contaminants are undesirable in that they frequently impart an objectionable taste or odor to the end product. Likewise, in the production of high polymers such as those employed in fiber manufacture, very small quantities of carbonyl contaminants cause an undesirable off color in the polymer and, even more important in most cases, act as so-called "chain stoppers" which prevent the formation of the desired long polymer chains.

The problem of carbonyl contamination in products of the types just discussed has been dealt with heretofore by methods which, with varying degrees of effectiveness, have included steam stripping (which usually entails the use of high vacuum and high steam consumption), solvent extraction (which is often not effective in removing the last traces of contamination which are still sufficient to cause problems), and chemical treatment such as the formation of bisulfite addition products (which frequently entails relatively complicated processing and which can itself introduce quality problems unless careful control methods are employed).

Thus, there remains a need for a carbonyl-removal method which is simple, effective, and economical.

It is, accordingly, an object of the present invention to provide a straightforward method for removing a carbonyl compound from a liquid containing said carbonyl compound as a solute. More particularly it is an object to provide a method for purifying an organic compound which is contaminated with an aldehyde or a ketone, especially an aldehyde. Other objects of the invention will be apparent from the following detailed description.

SUMMARY OF THE INVENTION

In accordance with the present invention a carbonyl compound is removed from a liquid in which it is dissolved by bringing the liquid into contact with solid polyvinyl alcohol. This, it has been found, results in adsorption or chemisorption of the carbonyl compound upon the solid polyvinyl alcohol surfaces with resulting abstraction of the carbonyl compound from the liquid. By passing the liquid through a bed of polyvinyl alcohol particles, one produces a purified effluent liquid which is extremely low in carbonyl content. When the adsorption capacity of the polyvinyl alcohol is exhausted (as indicated by a rise in the carbonyl content of the effluent liquid) the adsorption bed is either replaced or, optionally, regenerated by passing through it a warm aqueous acid solution followed by a water wash.

DETAILED DESCRIPTION OF THE INVENTION

Although it is not intended that this explanation be taken as a limitation on the scope of the present invention, it is believed that, when solid polyvinyl alcohol is brought into contact with a liquid containing a dissolved carbonyl compound, the carbonyl compound reacts chemically with hydroxy groups at or near the polyvinyl alcohol surface to form acetals (in the case of aldehydes) or ketals (in the case of ketones). Thus the carbonyl compound is retained on the polyvinyl alcohol in a manner analogous to conventional ion-exchange processes. Since the mechanism is one of chemisorption, however, as distinguished from pure adsorption in which an actual chemical reaction is not directly involved, the preparation of a specially-activated solid surface is not an essential part of the present process. That is, although high porosity, for example, is desirable for maximum adsorptive capacity in a given quantity of the polyvinyl alcohol, it is not essential. Therefore, any type of solid polyvinyl alcohol can be employed although types having a high surface:volume ratio are preferred (e.g. fine granules or beds of polyvinyl alcohol fiber).

Likewise, since chemical reaction between the carbonyl compound and the polyvinyl alcohol is at the heart of the present process, any compound having the carbonyl group, especially any aldehyde, can be removed by this method. The presence of substituent moieties in the molecule of the carbonyl compound is of no consequence since such moieties would either be inert toward the polyvinyl alcohol (in which case there is no ill effect) or else would react with it (in which case the present purpose has still been served even though the mechanism of the chemisorption might be different from the acetal or ketal formation characteristic of unsubstituted aldehydes or ketones).

The nature of the liquid from which the carbonyl contaminant is to be abstracted is a significant factor only to the extent that the liquid should be one in which polyvinyl alcohol is not soluble and which is chemically inert toward polyvinyl alcohol. It will be understood in this context, of course, that the carbonyl-contaminated compound which is to be purified need not necessarily be itself a liquid. For example, it can be a solid or even a gas, which is dissolved in a suitable inert solvent before being brought into contact with the polyvinyl alcohol. This same technique is also useful when the compound to be purified has a comparatively high melting point, admixture with a suitable liquid solvent thus obviating the need to carry out the present process at an elevated temperature. For example, monochlorobenzene is a useful solvent for bis(hydroxyethyl) terephthalate in this regard.

The liquid containing the carbonyl contaminant can be aqueous, but the adsorption process is more efficient with substantially anhydrous liquids. Although there is no sharp break point, increasing dryness in the liquid phase results in increasing efficiency in the adsorption process since water is a reaction product in the reaction between the carbonyl compound and the polyvinyl alcohol.

As explained above, the only essential requirement in the matter of the chemical identity of the materials to be purified (and in the nature of any solvents in which it may be desired to dissolve them prior to being contacted with the polyvinyl alcohol) is that they be chemically inert toward and nonsolvents for, the polyvinyl alcohol. Specific examples, however, include bis(hydroxyethyl) terephthalate, the propanediols, the butanediols (especially 1,3-butanediol which has extensive application in foodstuffs etc.), glycerine, and vinyl acetate. These are mentioned specifically because contamination by carbonyl compounds is a particular problem in processing them for many of their end uses.

Of the customarily-considered process parameters, pressure is of no consequence whatever so long as the pressure is high enough to keep the liquid being contacted with the polyvinyl alcohol in the liquid phase. Low temperatures (down to the temperature at which the liquid being processed solidifies) are preferable to elevated temperatures although at least some abstraction of the carbonyl compound from the liquid will take place even at substantially elevated temperature. Ambient temperatures (e.g., in the range of about 15° C to about 45° C) are entirely satisfactory and are recommended. Temperatures above about 100° C are not generally recommended, although it is possible, at the cost of reduction in adsorptive capacity of the adsorbent mass, to operate at even higher temperatures up that at which the type of polyvinyl alcohol being employed begins to soften.

Concentration of the carbonyl compound is a factor only to the extent that the higher the concentration the sooner the polyvinyl alcohol will become "loaded" and require replacement or regeneration. Exhaustion of the polyvinyl alcohol resulting from its becoming completely loaded with the carbonyl compound can be easily recognized, of course, by monitoring the purified effluent from the polyvinyl alcohol bed for carbonyl functionality by conventional analyses for the carbonyl group which are well known to chemists.

The pH of the liquid to be treated should preferably be adjusted, if necessary, to a value not higher than about 7.0, preferably about 5.0 to 6.9.

The adsorption reaction is very rapid, so that contact time of the liquid being treated with the solid polyvinyl alcohol bed is not a critical factor. It will be understood also, of course, that passage of the liquid to be purified through a fixed bed of the polyvinyl alcohol particles results in more efficient abstraction of the carbonyl compound from the liquid than when the liquid is simply mixed thoroughly with a suspension of the polyvinyl alcohol followed by separation therefrom by conventional methods such as filtration or decantation. Thus, it is recommended that the process be carried out by passing the liquid to be purified through a bed of polyvinyl alcohol particles (or packed fibers if desired) in a manner analogous to ion exchange processing or adsorption-type purification as with activated charcoal. Good results have been obtained, for example, by passing the liquid to be purified through a bed of polyvinyl alcohol particles at a rate of 10 to 20 volumes of liquid per volume of bed per hour, the bed being composed of particles approximately 0.5 millimeter in diameter.

When the adsorption bed has become loaded to capacity with the carbonyl compound (as evidenced by appearance of an undesired level of carbonyl compound in the purified effluent liquid) the bed can either be replaced with fresh material or, alternatively, it can be regenerated by passing a warm aqueous solution of a mineral acid through it to decompose the acetals. The regenerated bed is then washed with pure water, drained, and re-used. Typically, however, carbonyl contamination of the type which constitutes a quality problem in the materials to which this invention is primarily directed is at a very low level, such that it is usually feasible to discard the polyvinyl alcohol and replace it with fresh material.

It will be understood that polyvinyl alcohol is available in several grades varying in, for example, polymer chain length. All solid polyvinyl alcohol, regardless of type, exhibits the carbonyl abstraction effect on which the present process is based. If, however, regeneration of the polyvinyl alcohol is contemplated, care should be taken to select one of the higher molecular weight types which are not soluble in hot water, inasmuch as regeneration entails contacting the polyvinyl alcohol with a warm or hot aqueous solution of an acid. Solubility of a given type of polyvinyl alcohol in hot water or in aqueous acid can readily be determined experimentally.

The following example is given to illustrate the invention further. It will be recognized that many variations can be made therefrom within the scope of the invention.

EXAMPLE I

Fifteen grams of polyvinyl alcohol powder was mixed with monochlorobenzene to form a slurry containing about 30% solids. The slurry was then poured into a vertical cylindrical vessel 11 millimeters in diameter and allowed to settle into a bed of polyvinyl alcohol particles approximately 34 centimeters deep. A solution containing 1.0 gram of benzaldehyde dissolved in 200 grams of monochlorobenzene was then passed through the polyvinyl alcohol bed at about 5 ml per minute until the pure monochlorobenzene initially present as a component of the slurry had been displaced from the bed.

As soon as the initial charge of pure monochlorobenzene had been displaced, and with the benzaldehyde solution still being continuously passed through the bed at 5 ml per minute, 10 ml fractions of the emerging purified liquid were collected in the order of their emergence and analyzed (by chromatographic methods) for benzaldehyde content. The first eight fractions collected contained water (not present in the solution when it was introduced into the bed) but no detectable quantity of benzaldehyde. The ninth fraction contained about 0.05% benzaldehyde, and the tenth and all subsequent fractions contained no water and the same amount of benzaldehyde as was contained in the liquid being introduced into the bed.

Thus it will be seen that benzaldehyde abstraction was very effective, with no appreciable decline in the efficiency of the benzaldehyde abstraction, up until the time when exhaustion of the bed resulted in a sudden drop in abstraction efficiency. The fifteen grams of polyvinyl alcohol had taken up about 0.45 gram of benzaldehyde.

The embodiments of the invention in which an exclusive property or privilege is claimed are defined as follows:

1. A method for removing an aldehyde contaminant from a liquid member of the group consisting of monochlorobenzene; the propanediols; the butanediols; vinyl acetate; glycerine; bis-(hydroxyethyl) terephthalate; and mixtures of bis-(hydroxyethyl) terephthalate with an inert solvent, which method comprises passing said liquid through a liquid-permeable bed of solids consisting essentially of polyvinyl alcohol and adsorbing said aldehyde upon said solids at a temperature which is between that at which said polyvinyl alcohol begins to soften and that at which said liquid solidifies.

2. The method of claim 1 wherein said temperature is below about 100° C.

3. A method for removing an aldehyde contaminant from a liquid member of the group consisting of monochlorobenzene; the propanediols; the butanediols; vinyl acetate; glycerine; bis-(hydroxyethyl) terephthalate;

and mixtures of bis-(hydroxyethyl) terephthalate with chlorobenzene, which method comprises passing said liquid through a liquid-permeable bed of solids consisting essentially of polyvinyl alcohol and adsorbing said aldehyde upon said solids at a temperature which is between that at which said polyvinyl alcohol begins to soften and that at which said liquid solidifies.

4. The method of claim 3 wherein said temperature is below about 100° C.

5. A method for removing an aldehyde contaminant from liquid chlorobenzene, which method comprises passing said chlorobenzene through a liquid-permeable bed of solids consisting essentially of polyvinyl alcohol and adsorbing said aldehyde upon said solids at a temperature below about 100° C.

* * * * *